UNITED STATES PATENT OFFICE.

JOHN M. PERKINS, OF ASBURY, NEW JERSEY, ASSIGNOR TO R. R. PERKINS, OF SAME PLACE.

IMPROVEMENT IN CARPET-LININGS.

Specification forming part of Letters Patent No. 76,342, dated April 7, 1868; reissue No. 6,795, dated December 14, 1875; application filed June 9, 1875.

*To all whom it may concern:*

Be it known that I, JOHN M. PERKINS, of Asbury, in Warren county and State of New Jersey, have invented a new and useful improvement in the combination of wood, paper, or textile fabric for aromatic linings for carpets, chests, and other articles.

Such aromatic articles will impart a pleasant odor to the dwelling, and will be of great value in repelling moths and other insects destructive to woolen and fur goods, and many other annoying insects to which dwelling rooms are subject; and I hereby declare the following to be a full, clear, and exact description of the same, which will enable the public to fully understand my invention, and those skilled in the art to construct and use it.

I take a section or log of camphor, cedar, or other aromatic wood, which, from the pungency of the ordor emitted therefrom, is found to repel moths or other insects, whose ravages are destructive or injurious to woolen, fur, and other goods, and other troublesome insects, and having shaved, turned, or otherwise obtained from said log or section a thin lamina or veneer, I proceed to apply to one side of said veneer a lining of paper, paper pulp, or cloth for the purpose of giving greater strength to my said lamina to enable it to withstand more perfectly the wear and tear to which it would be subjected. I unite the lamina with paper, paper-pulp, or textile fabric, either in the paper-mill in the process of fabricating the said paper, or by attaching the already-formed paper or cloth to the lamina by adhesive material.

The ordinary and well-known method of protecting wool, and fur, and fur goods, feathers, &c., from the ravages of insects is to scatter upon carpets, or to intersperse with the goods to be protected, aromatic drugs, gums, or leaves, as the aromatic gum of camphor-tree, the leaves of the tobacco-plant, &c., or to place the goods in costly boxes or chests made from aromatic woods.

The first method is unclean and unsightly; the second too expensive for general use. By my method I obviate both of these objections, and in the case of carpets secure a more perfect result, the aroma so offensive to the moth arising from the lining and permeating every fiber of the carpet, while in the case of boxes or chests I am enabled to ornament the interior walls, as well as to secure a permanent aroma, for the purpose indicated at a trifling expense.

My object is to secure the aromatic effect without the unsightliness necessary in bestrewing the articles to be protected, and without the costliness of solid chests of aromatic woods, and at the same time to render my application of the repelling aroma ornamental as well as useful, when applied as lining for carpets by protecting it from wear from the roughness and inequalities of the floor.

What I claim as new, and desire to secure by Letters Patent, is—

A lining, consisting of a sheet of aromatic wood, combined with textile fabric or paper applied to the surface or surfaces of said wood, substantially as and for the object specified.

JOHN M. PERKINS.
R. R. PERKINS,
*Assignee.*

Witnesses:
LEWIS H. WIEDER,
GEORGE W. WOOLLEY, Jr.